(12) United States Patent
Komiyama et al.

(10) Patent No.: US 10,743,757 B2
(45) Date of Patent: Aug. 18, 2020

(54) ULTRASONIC TRANSDUCER

(71) Applicant: NIHON DEMPA KOGYO CO., LTD., Tokyo (JP)

(72) Inventors: Kazuhiko Komiyama, Saitama (JP); Yasunobu Hasegawa, Saitama (JP)

(73) Assignee: NIHON DEMPA KOGYO CO., LTD., Tokyo (JP)

( * ) Notice: Subject to any disclaimer, the term of this patent is extended or adjusted under 35 U.S.C. 154(b) by 183 days.

(21) Appl. No.: 16/125,782

(22) Filed: Sep. 10, 2018

(65) Prior Publication Data
US 2019/0090734 A1    Mar. 28, 2019

(30) Foreign Application Priority Data
Sep. 28, 2017 (JP) .................................. 2017-187485

(51) Int. Cl.
| | |
|---|---|
| *A61B 3/10* | (2006.01) |
| *A61B 3/00* | (2006.01) |
| *G01N 29/28* | (2006.01) |
| *G01N 29/24* | (2006.01) |
| *A61B 8/00* | (2006.01) |
| *A61B 8/10* | (2006.01) |

(52) U.S. Cl.
CPC .......... *A61B 3/1005* (2013.01); *A61B 3/0008* (2013.01); *A61B 8/10* (2013.01); *A61B 8/4281* (2013.01); *A61B 8/4416* (2013.01); *A61B 8/4483* (2013.01); *A61B 8/4494* (2013.01); *G01N 29/2437* (2013.01); *G01N 29/28* (2013.01)

(58) Field of Classification Search
CPC .......... A61B 3/0008; A61B 17/320068; A61B 2017/00106; A61B 5/0095; A61B 8/10; A61B 8/00; A61B 8/4281; A61B 8/4477
USPC .................................................. 351/221, 246
See application file for complete search history.

(56) References Cited

U.S. PATENT DOCUMENTS

2015/0150456 A1\* 6/2015 Brennan ............... A61M 25/01
600/427

FOREIGN PATENT DOCUMENTS

| JP | 2000139926 | 5/2000 |
|---|---|---|
| JP | 2000157545 | 6/2000 |
| JP | 2005296536 | 10/2005 |
| JP | 2009247416 | 10/2009 |

(Continued)

*Primary Examiner* — Hung X Dang
(74) *Attorney, Agent, or Firm* — JCIPRNET (57) ABSTRACT

An ultrasonic transducer includes a piezoelectric element in round shape, an acoustic lens, and an acoustic matching layer. The piezoelectric element generates an ultrasonic sound wave. The acoustic matching layer decreases a reflection of the ultrasonic sound wave from a subject. The piezoelectric element has a center having a hole through which an optical fiber that guides a light of a light source passes. The ultrasonic transducer transmits and receives the ultrasonic sound wave while emitting the light. The acoustic lens has a material using a resin with a withstand voltage, mainly polymethylpentene. The acoustic matching layer has a thickness set to λ/4 by not applying a polyparaxylylene coating for ensuring the withstand voltage on the acoustic matching layer. The optical fiber has a distal end configured not to pass through the acoustic lens. The piezoelectric element and the acoustic matching layer have shapes in a planar surface.

3 Claims, 5 Drawing Sheets

(56) References Cited

FOREIGN PATENT DOCUMENTS

JP 2016025612 2/2016

* cited by examiner

ULTRASONIC TRANSDUCER

CROSS-REFERENCE TO RELATED APPLICATIONS

This application is based on and claims priority under 35 U.S.C. § 119 to Japanese Patent Application No. 2017-187485, filed on Sep. 28, 2017, the entire content of which is incorporated herein by reference.

TECHNICAL FIELD

This disclosure relates to an ultrasonic transducer.

DESCRIPTION OF THE RELATED ART

An ultrasonic transducer has been widely used for a transmitting/receiving section of an ultrasonic diagnostic device for an ultrasonic sound wave (for example, see Japanese Unexamined Patent Application Publication No. 2016-025612 and Japanese Unexamined Patent Application Publication No. 2009-247416). There is an ultrasonic transducer that transmits an ultrasonic sound wave while contacting a cornea surface and measures an ocular axial length (a length from a surface of an eye/a cornea to a back of the eye/a retina=a diameter of an eyeball) from a propagation time of the reflected wave. This ultrasonic transducer for measuring the ocular axial length is used by directly touching an eyeball. Accordingly, it is necessary to ensure protecting, for example, a cornea of the eyeball and relieving a pain of a subject when the ultrasonic transducer touches the eyeball. In view of this, an abutting surface of the ultrasonic transducer that abuts on the eyeball is preferred to be formed smooth without a local unevenness.

Japanese Unexamined Patent Application Publication No. 2000-157545 discloses a configuration in which a transducer main body made of a piezoelectric element and an acoustic matching layer is projected from a transducer case as an ultrasonic transducer for measuring an ocular axial length that prioritizes a safety for not damaging a surface of an eyeball. In this configuration of the ultrasonic transducer, both of a piezoelectric element and an acoustic matching layer have a curved shape having a depressed surface. On an ultrasonic sound wave transmitting and receiving surface of a transducer main body including a front surface of an acoustic matching layer, a protective coating that uses polyparaxylylene as a main raw material is formed. Japanese Unexamined Patent Application Publication No. 2000-157545 discloses a configuration in which a light emitting diode is disposed on a back surface side of the transducer main body and a measurement is performed by transmitting and receiving an ultrasonic sound wave with irradiating the eyeball with a light of this light emitting diode via an optical fiber as an exemplary related art.

Medical equipment is required to have a predetermined withstand voltage from an aspect of ensuring its safety. Since an ultrasonic transducer is abutted on a subject and used, it is also required to have a biocompatibility. Furthermore, since an ultrasonic transducer is sterilized, a chemical resistance is required for a durability of an ultrasonic transducer. Accordingly, for example, in the ultrasonic transducer having the configuration disclosed in Japanese Unexamined Patent Application Publication No. 2000-157545, which is a part of medical equipment, it has been necessary to take an action to ensure the withstand voltage by forming an acoustic matching layer into a predetermined thickness or forming a protective coating on a surface of the acoustic matching layer. In the ultrasonic transducer disclosed in Japanese Unexamined Patent Application Publication No. 2000-157545, it has been necessary to form a piezoelectric element and an acoustic matching layer into a curved shape having a curved surface with a predetermined curvature for converging the ultrasonic sound wave. In view of this, a limitation of freedom in designing the ultrasonic transducer has been caused since there is a case where it is not possible to set a thickness of the acoustic matching layer to a desired thin thickness and form the piezoelectric element and the acoustic matching layer into a desired shape. Forming the above-described protective coating involves a relatively high cost, therefore causing an increased cost for producing the ultrasonic transducer.

Furthermore, among the ultrasonic transducers having a configuration in which an eyeball is irradiated with a light via an abutting surface with the eyeball, the ultrasonic transducer in which a light guiding member, such as an optical fiber, is disposed up to the abutting surface and the ultrasonic transducer in which the light guiding member is disposed up to proximity of the abutting surface, such as a near side of the protective coating, needed to be produced by accurately assembling components of the ultrasonic transducer such that a presence of the light guiding member does not generate a level difference and a local unevenness on the abutting surface to inhibit the smoothness of the abutting surface.

A need thus exists for an ultrasonic transducer which is not susceptible to the drawback mentioned above.

SUMMARY

According to an aspect of this disclosure, there is provided an ultrasonic transducer including a piezoelectric element in round shape, an acoustic lens, and an acoustic matching layer. The piezoelectric element generates an ultrasonic sound wave having a wavelength $\lambda$. The acoustic lens converges the ultrasonic sound wave. The acoustic matching layer decreases a reflection of the ultrasonic sound wave from a subject. The piezoelectric element has a center having a hole through which an optical fiber that guides a light of a light source passes. The ultrasonic transducer transmits and receives the ultrasonic sound wave while emitting the light. The acoustic lens has a material using a resin with a withstand voltage, mainly polymethylpentene. The acoustic matching layer has a thickness set to $\lambda/4$ by not applying a polyparaxylylene coating for ensuring the withstand voltage on the acoustic matching layer. The optical fiber has a distal end configured not to pass through the acoustic lens. The piezoelectric element and the acoustic matching layer have shapes in a planar surface.

BRIEF DESCRIPTION OF THE DRAWINGS

The foregoing and additional features and characteristics of this disclosure will become more apparent from the following detailed description considered with reference to the accompanying drawings, wherein.

DETAILED DESCRIPTION

The following describes embodiments with reference to the drawings. Note that this disclosure is not limited to these embodiments. In addition, the drawings are appropriately scaled, for example, partially enlarged or highlighted to describe the embodiments.

Figure 1:
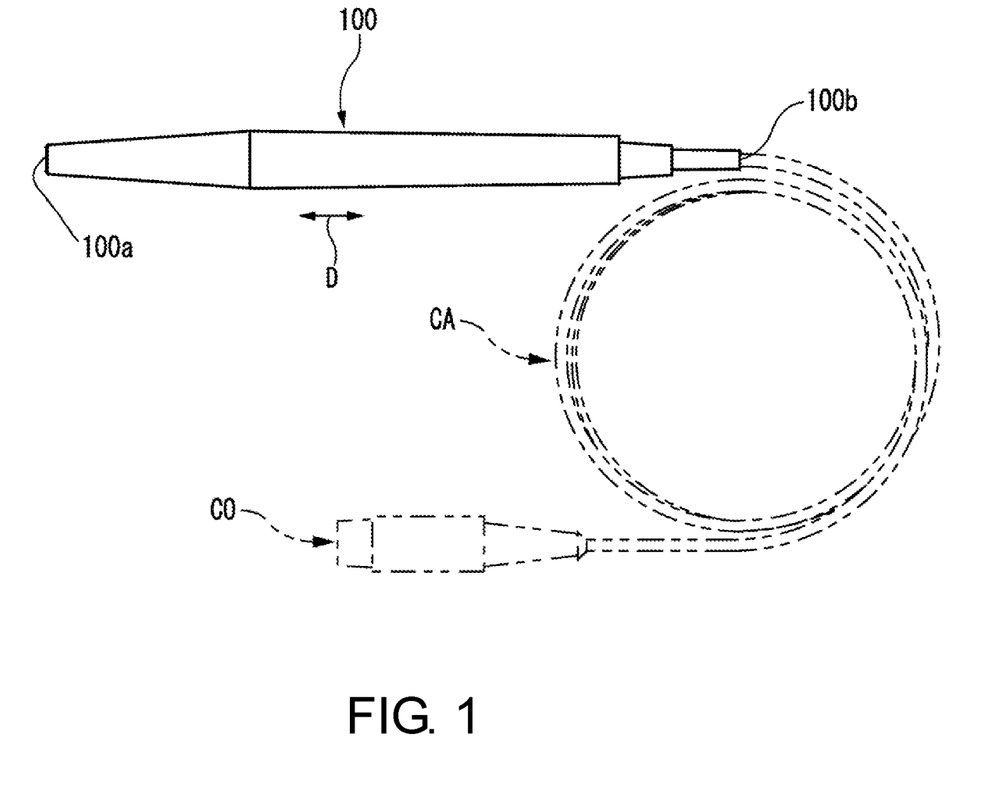
FIG. 1 is a side view illustrating an exemplary ultrasonic transducer according to an embodiment of the disclosure.

FIG. 1 is a side view illustrating an exemplary overall configuration of an ultrasonic transducer 100 according to the embodiment. As illustrated in FIG. 1, the ultrasonic transducer 100 is formed into an elongated rod shape.

The ultrasonic transducer 100 is used as a transmitting/receiving section of an ultrasonic diagnostic device for an ultrasonic sound wave. In this ultrasonic diagnostic device, the ultrasonic transducer 100 is electrically connected to an ultrasonic diagnostic device main body (not illustrated) via a cable CA and a connecting terminal CO. The ultrasonic transducer 100 has a base end portion (the right-side end portion of the ultrasonic transducer 100 in FIG. 1) 100b is connected to the cable CA. A power source for operating the ultrasonic transducer 100 is supplied to the ultrasonic transducer 100 via the cable CA from the ultrasonic diagnostic device main body. The ultrasonic transducer 100 transmits an ultrasonic sound wave to a subject and receives the ultrasonic sound wave reflected by the subject, and converts the reflected ultrasonic sound wave into an electrical signal. The ultrasonic transducer 100 then transmits the electrical signal to the ultrasonic diagnostic device main body via the cable CA.

Figure 2:
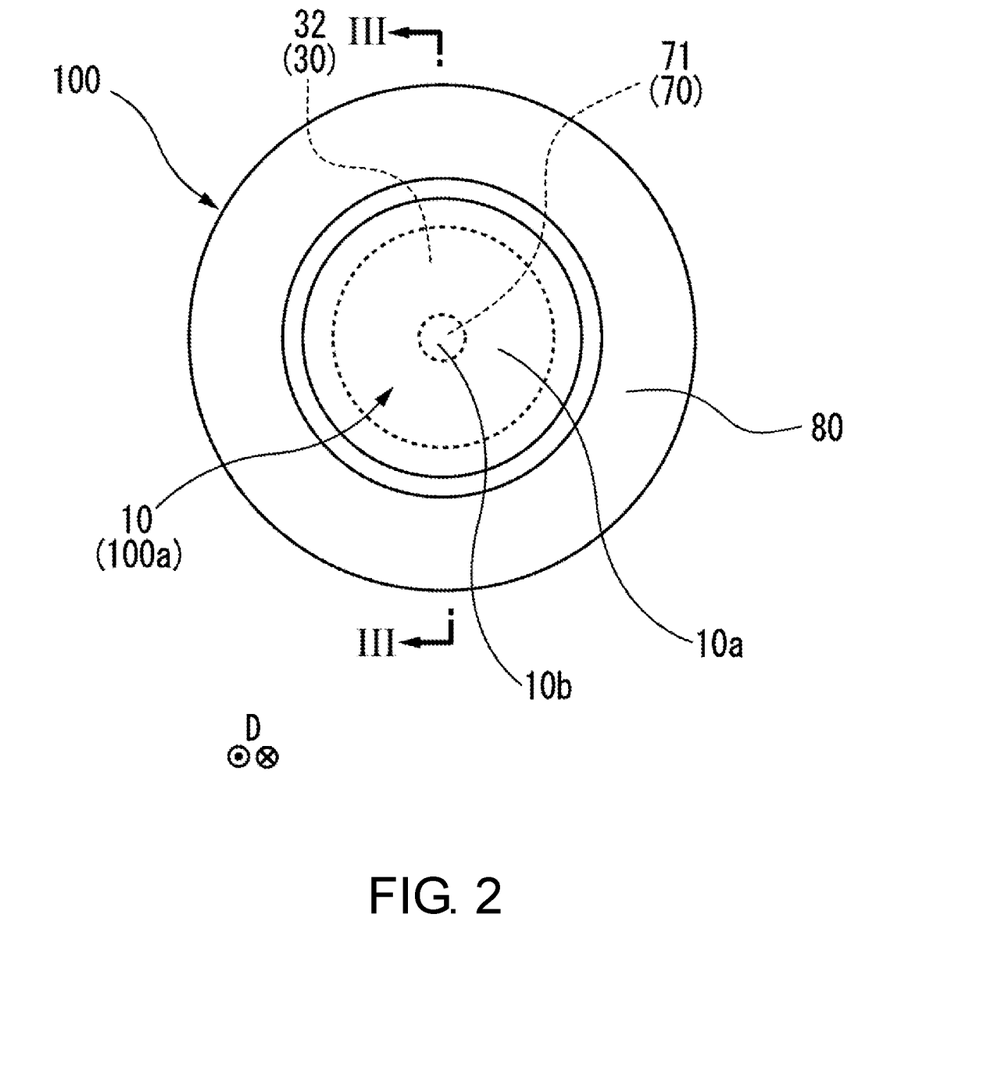
FIG. 2 is a front view of the ultrasonic transducer in FIG. 1.

FIG. 2 is a front view of the ultrasonic transducer 100 and is a drawing when the ultrasonic transducer 100 is viewed from a side of a distal end 100a (a front). As illustrated in FIG. 2, an outer shape of the ultrasonic transducer 100 viewed from the distal end 100a side is in a substantially perfect circle shape.

The ultrasonic diagnostic device including such ultrasonic transducer 100 is mainly used for measuring an ocular axial length of an eyeball. In this case, the subject is the eyeball. However, this ultrasonic diagnostic device may be one that has a usage other than measuring the ocular axial length. The ultrasonic transducer 100 according to the embodiment is, for example, an ultrasonic transducer for measuring the ocular axial length, and is used by directly abutting an abutting surface 10 on the distal end 100a of the ultrasonic transducer 100 onto the eyeball. The abutting surface 10 is formed so as to abut on the eyeball as the subject and abuts on the eyeball when the ocular axial length is measured. When the ocular axial length of the eyeball is measured using the above-described ultrasonic diagnostic device, the ultrasonic transducer 100 transmits an ultrasonic sound wave toward the eyeball and receives the ultrasonic sound wave reflected by the eyeball. The ultrasonic transducer 100 also emits a light toward the eyeball when the ocular axial length is measured. The abutting surface 10 includes an ultrasonic sound wave transmitting and receiving surface 10a that transmits and receives the ultrasonic sound wave and a light emission surface 10b that emits the light.

Figure 3:
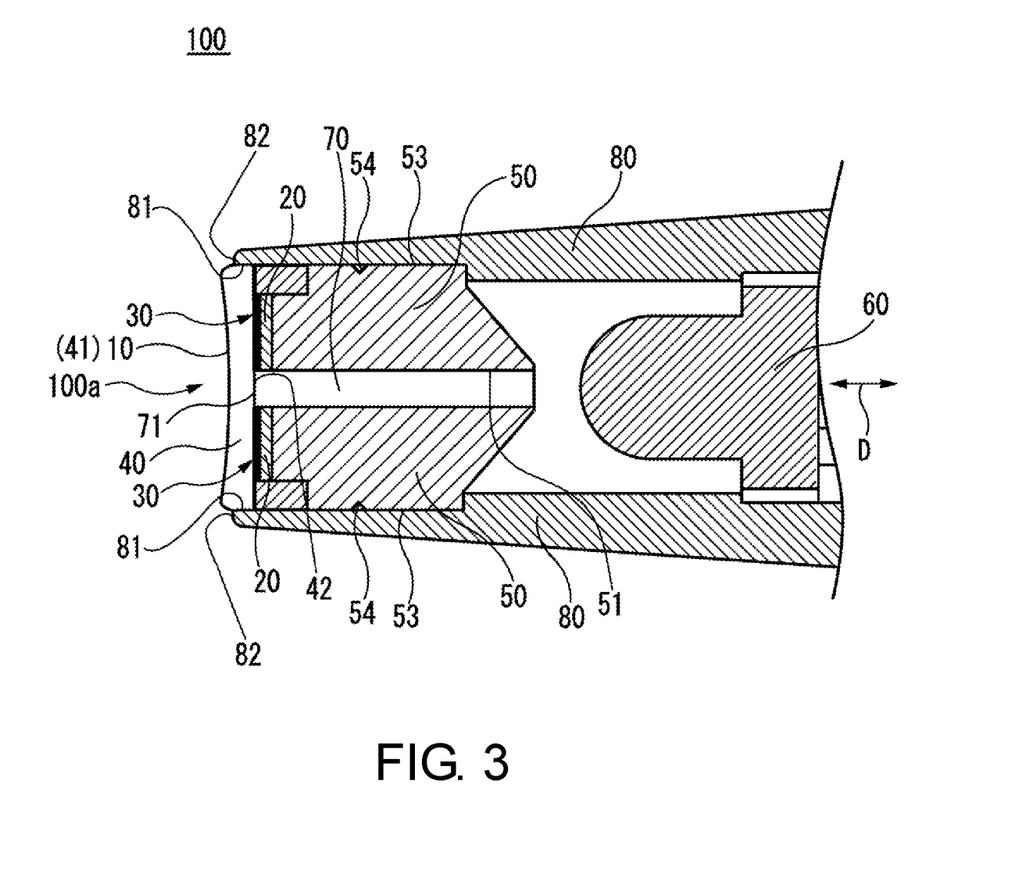
FIG. 3 is a main part sectional drawing taken along a line in FIG. 2.

FIG. 3 is a main part sectional drawing of the ultrasonic transducer 100 and illustrates a main part of a sectional drawing taken along a line (a line passing through a center portion of the abutting surface 10 of the ultrasonic transducer 100 and extending in an axial direction D) in FIG. 2. As illustrated in FIG. 3, the ultrasonic transducer 100 is constituted by including a piezoelectric element 20, an acoustic matching layer 30, an acoustic lens 40, a backing material 50, a light source 60, an optical fiber 70, and a transducer case 80.

Figure 4:
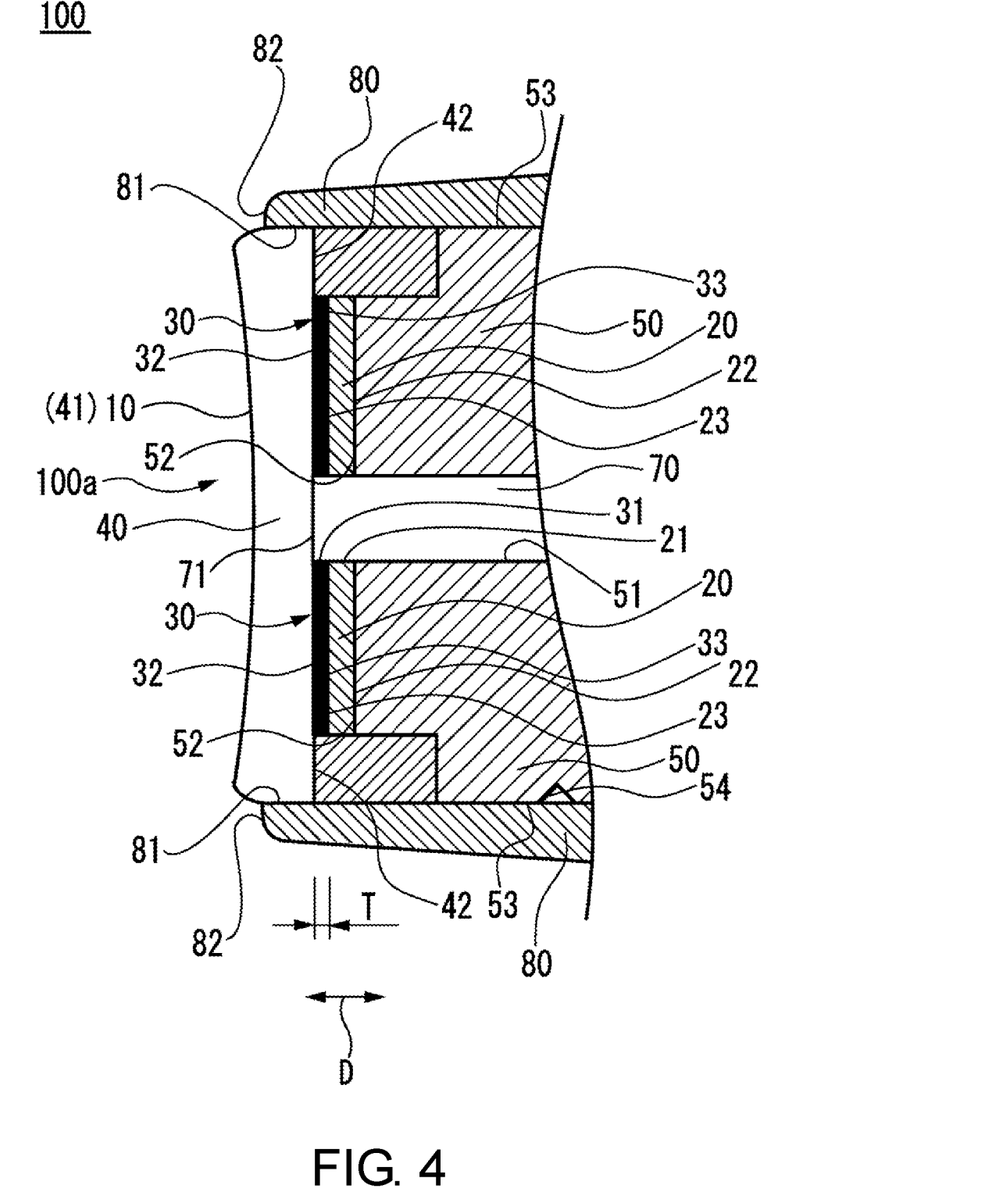
FIG. 4 is a partially enlarged figure of FIG. 3.

FIG. 4 is a partially enlarged figure of FIG. 3 and is a drawing that enlarges a portion of the distal end 100a of the ultrasonic transducer 100 in FIG. 3. As illustrated in FIG. 3 and FIG. 4, the piezoelectric element 20 is housed in the transducer case 80. The piezoelectric element 20 is fixedly secured to a front surface (a surface on a distal end side) 52 of the backing material 50 with, for example, an adhesive. The piezoelectric element 20 has a rear surface (a surface on a base end side) 22 that is a bonding surface bonded on the front surface 52 of the backing material 50. The piezoelectric element 20 has a front surface (a surface on the distal end side) 23 that is a bonding surface bonded on a rear surface 33 of the acoustic matching layer 30. The piezoelectric element 20 is in, what is called, a round shape, and is formed into a disk shape of a perfect circle shape having a thickness direction in the axial direction D of the ultrasonic transducer 100. Both end surfaces (principal surfaces) 22 and 23 in the thickness direction of the piezoelectric element 20 are in a planar surface. The piezoelectric element 20 has a piezoelectric property and formed of a piezoelectric material. The piezoelectric element 20 is formed of lead zirconate titanate (PZT) or a material whose main component is PZT. PZT is a piezoelectric ceramic and is one of the materials having a relatively high piezoelectric efficiency.

Both end surfaces 22 and 23 in the thickness direction of the piezoelectric element 20 include respective electrodes (not illustrated). Applying a predetermined A.C. voltage to this electrode generates an ultrasonic sound wave in the piezoelectric element 20. The piezoelectric element 20 receives the ultrasonic sound wave reflected by the eyeball as the subject and converts the received ultrasonic sound wave into an electrical signal.

Both end surfaces 22 and 23 in the thickness direction of the piezoelectric element 20 have central portions that have a first hole (a hole) 21 passing through the piezoelectric element 20 in the thickness direction. The first hole 21 is formed such that the optical fiber 70 can be inserted through. The first hole 21 has a cross-sectional shape in, for example, a shape identical to a cross-sectional shape of the optical fiber 70. The cross-sectional surface of the first hole 21 has an area that is set to be, for example, slightly wider than an area of the cross-sectional surface of the optical fiber 70.

The acoustic matching layer 30 is a layer for matching acoustic characteristics of the piezoelectric element 20 and the eyeball as the subject. The acoustic matching layer 30 is used for efficiently transmitting the ultrasonic sound wave through the eyeball. That is, the acoustic matching layer 30 is disposed in order to decrease a reflection of the ultrasonic sound wave on a surface of the eyeball when the ultrasonic sound wave is transmitted toward the eyeball from the ultrasonic transducer 100.

The acoustic matching layer 30 is disposed in a front side (a side of the ultrasonic sound wave transmitting and receiving surface 10a) of the piezoelectric element 20. The acoustic matching layer 30 has a front surface (a surface on the distal end side) 32 that is a bonding surface bonding with a rear surface (a surface on the base end side) 42 of the acoustic lens 40. The acoustic matching layer 30 has a rear surface (a surface on the base end side) 33 that is a bonding surface bonding with the front surface 23 of the piezoelectric element 20. The acoustic matching layer 30 is formed into a disk shape of a perfect circle shape having a thickness direction in a direction (the axial direction D of the ultrasonic transducer 100) in which the ultrasonic sound wave is transmitted. Both end surfaces 32 and 33 in the thickness direction are in a planar surface. The acoustic matching layer 30 is disposed so as to be laminated in the thickness direction with respect to the piezoelectric element 20.

The acoustic matching layer 30 is formed of an epoxy resin. Note that the acoustic matching layer 30 can be formed of various kinds of materials, not limited to the epoxy resin. The acoustic matching layer 30 may be in a single layer structure or may be in a laminated structure.

The acoustic matching layer 30 has a predetermined thickness T in a direction in which the ultrasonic sound wave is transmitted. When a wavelength of the ultrasonic sound wave transmitted through the acoustic matching layer 30 is $\lambda$, the thickness T is set to be $\lambda/4$. Here, the thickness T is set from a frequency of the ultrasonic sound wave and the material of the piezoelectric element 20, and the wavelength $\lambda$ is v/f when the acoustic matching layer 30 has an acoustic velocity of v and a frequency of f. For example, when v=2200 m/s and f=10 MHz, the wavelength $\lambda$ is 220 µm and the thickness T is 55 µm, a quarter of the wavelength $\lambda$.

Both end surfaces (principal surfaces) 32 and 33 in the thickness direction of the acoustic matching layer 30 have central portions that have a second hole 31 passing through the acoustic matching layer 30 in the thickness direction. The second hole 31 communicates with the first hole 21 and a third hole 51 described later. The second hole 31 is formed such that the optical fiber 70 can be inserted through, similarly to the first hole 21. The second hole 31 has a cross-sectional shape in, for example, a shape identical to the cross-sectional shape of the optical fiber 70. The cross-sectional surface of the second hole 31 has an area that is set to be, for example, slightly wider than the area of the cross-sectional surface of the optical fiber 70. Note that the second hole 31 is not necessarily disposed in the acoustic matching layer 30. When the second hole 31 is not disposed, the acoustic matching layer 30 may be formed to be transparent or semitransparent so as to transmit the light emitted from the optical fiber in the thickness direction of the acoustic matching layer 30.

The acoustic lens 40 is formed in the distal end 100a portion of the ultrasonic transducer 100. The acoustic lens 40 has the abutting surface 10. The abutting surface 10 is abutted on the eyeball when the ocular axial length is measured using the ultrasonic transducer 100 as described above.

The abutting surface 10 is also a front surface (a surface on the distal end side) 41 of the acoustic lens 40 and positioned on the distal end 100a of the ultrasonic transducer 100. The abutting surface 10 includes the ultrasonic sound wave transmitting and receiving surface 10a with which the ultrasonic sound wave is transmitted and received and the light emission surface 10b from which the light is emitted as described above (see FIG. 2).

The abutting surface 10 has a depressed-shaped curved surface. Accordingly, the abutting surface 10 has a shape that fits well to a curved surface of the eyeball as the subject compared with a case where the abutting surface 10 is formed into a convex-shaped surface, a planar surface, and similar shaped surface. The ultrasonic sound wave transmitting and receiving surface 10a and the light emission surface 10b are formed on an identical surface. Since the abutting surface 10 is in the depressed-shaped curved surface in this embodiment, the ultrasonic sound wave transmitting and receiving surface 10a and the light emission surface 10b are formed on an identical curved surface.

The acoustic lens 40 converges the ultrasonic sound wave transmitted from the ultrasonic transducer 100. In view of this, the ultrasonic sound wave transmitting and receiving surface 10a has a concave-shaped curved surface set to have a predetermined curvature. A region of the ultrasonic sound wave transmitting and receiving surface 10a on the abutting surface 10 is approximately identical to a region of the acoustic matching layer 30 in a view of the axial direction D of the ultrasonic transducer 100 (see FIG. 2).

The front surface 41 (the abutting surface 10) of the acoustic lens 40 has an outer shape in a perfect circle shape when viewed from the axial direction D of the ultrasonic transducer 100. The rear surface (a principal surface on an opposite side to the front surface 41) 42 of the acoustic lens 40 is a perfect circle shaped planar surface. Note that, the front surface 41 and the rear surface 42 of the acoustic lens 40 are not limited to be in the perfect circle shape, but may be in, for example, an elliptical shape, an oval shape, and a polygon. A surface shape of the abutting surface 10 is not limited to a depressed surface shape, but may be, for example, a planar surface shape and a gentle protruding surface shape.

The acoustic lens 40 is disposed on a front side (the distal end 100a side of the ultrasonic transducer 100) of the acoustic matching layer 30. The acoustic lens 40 is disposed so as to be partly overlapped in the thickness direction on the acoustic matching layer 30. The rear surface 42 of the acoustic lens 40 has a part bonded on the bonding surface 32 of the acoustic matching layer 30. The acoustic lens 40 is disposed on a front side (the distal end side) of the optical fiber 70. The optical fiber 70 does not pass through the acoustic lens 40. The abutting surface 10 is spaced from the optical fiber 70. While the rear surface 42 of the acoustic lens 40 abuts on a distal end 71 of the optical fiber 70, the rear surface 42 of the acoustic lens 40 may be spaced from the optical fiber 70. The acoustic lens 40 is secured such that the acoustic lens 40 is fitted in an opening portion 81 formed in the distal end portion of the transducer case 80. The distal end portion of the acoustic lens 40 including the abutting surface 10 projects forward with respect to a distal end 82 of the transducer case 80 and is formed into a size with which the abutting surface 10 can abut on the eyeball as the subject.

A region of the light emission surface 10b in the abutting surface 10 is approximately identical to a region of the distal end 71 of the optical fiber 70 in a view of the axial direction D of the ultrasonic transducer 100 (see FIG. 2). Note that, in the abutting surface 10, the region of the light emission surface 10b may be partly overlapped on the region of the ultrasonic sound wave transmitting and receiving surface 10a or may be a region different from the region of the ultrasonic sound wave transmitting and receiving surface 10a.

Since the acoustic lens 40 abuts on the eyeball, a material that is less likely to cause the foreign body reaction (having a biocompatibility) when the acoustic lens 40 abuts on an eyeball of a living body is used for the acoustic lens 40. The acoustic lens 40 is formed of a resin having a withstand voltage (insulation property). The acoustic lens 40 has a thickness in the axial direction D of the ultrasonic transducer 100. The thickness of the acoustic lens 40 is set such that the ultrasonic transducer 100 has a predetermined withstand voltage. In the ultrasonic transducer 100, in particular, the withstand voltage in a portion inside the opening portion 81 of the transducer case 80 is ensured by a configuration that includes the above-described acoustic lens 40. That is, in the embodiment, as described above, the acoustic matching layer 30 is set to be $\lambda/4$ so as to be thinly formed; even though a protective coating, such as a polyparaxylylene coating, is not formed on the front surface of the ultrasonic transducer 100, the resin having the withstand voltage (insulation property) is adopted for the acoustic lens 40; and adjusting the thickness of the acoustic lens 40 ensures the withstand voltage of the ultrasonic transducer 100.

Polymethylpentene (PMP) is used for a resin material constituting the acoustic lens 40. The polymethylpentene is a plastic having a relatively small specific gravity. This configuration ensures relatively decreasing the acoustic impedance of the acoustic lens 40 and this ensures increasing transmission efficiency of the ultrasonic sound wave in the acoustic lens 40. The polymethylpentene is a transparent resin, thus, the acoustic lens 40 is transparent. This configuration ensures efficiently transmitting the light emitted from the distal end 71 of the optical fiber 70 in the acoustic lens 40 up to the light emission surface 10b. Furthermore, the polymethylpentene has a chemical resistance and, thus, the acoustic lens 40 has the chemical resistance. Even in a case where chemicals, such as an antiseptic solution, is used, for example, when the abutting surface 10 is cleaned, this configuration ensures reducing a deterioration of the acoustic lens 40 caused by the chemicals.

Note that the acoustic lens 40 may be formed only of the polymethylpentene or may be formed of a material whose main component is the polymethylpentene. The acoustic lens 40 may be formed of a material whose main component is a material other than the polymethylpentene or may be formed by using another resin material, such as a silicon rubber, without including the polymethylpentene. The acoustic lens 40 is not limited to be transparent, but may be semitransparent. When the acoustic lens 40 is semitransparent, the acoustic lens 40 has a translucency to the extent that causes the light emitted from the distal end 71 of the optical fiber 70 to reach the light emission surface 10b.

The backing material 50 is fixedly secured to the transducer case 80 in a state of being housed in the transducer case 80. The piezoelectric element 20 is fixedly secured to the front surface 52 of the backing material 50. This configuration causes the backing material 50 to reduce an occurrence of an extra vibration of the piezoelectric element 20. The backing material 50 has, for example, a shape including a substantially cylindrical shape with the axial direction D of the ultrasonic transducer 100 as a height direction and is, for example, a rubber-based resin. The backing material 50 has a side peripheral surface 53 on which grooves 54 and 54 are formed in order to dispose an adhesive. When the backing material 50 is fixedly secured into an inside of the transducer case 80, the adhesive is applied in the grooves 54 and 54 before the backing material 50 is inserted into the inside of the transducer case 80. The groove 54 has a cross-sectional shape in a V shape.

The backing material 50 has the third hole 51 passing through the backing material 50 in the axial direction D in a central portion in the view of the axial direction D of the ultrasonic transducer 100 (view of the height direction). The third hole 51 communicates with the first hole 21 and the second hole 31. The third hole 51 is formed such that the optical fiber 70 can be inserted through, similarly to the first hole 21 and the second hole 31. The third hole 51 has a cross-sectional shape in, for example, a shape identical to the cross-sectional shape of the optical fiber 70. The cross-sectional surface of the third hole 51 has an area that is set to be, for example, slightly wider than the area of the cross-sectional surface of the optical fiber 70. Each of the first hole 21, the second hole 31, and the third hole 51 is in an identical shape and an identical size and formed to overlap on one another when viewed in the axial direction D of the ultrasonic transducer 100.

The light source 60 is housed in the transducer case 80 and disposed, for example, in the base end side of the optical fiber 70. The light source 60 generates a light emitted via the light emission surface 10b of the ultrasonic transducer 100. The light source 60 is, for example, a light emitting diode (LED) lamp. The base end portion (a rear portion) of the light source 60 is electrically connected to the power source (not illustrated). An electric power supply from this power source to the light source 60 causes the light source 60 to emit a light. The light source 60 emits a light toward the optical fiber 70 in the distal end direction (a font side) of the light source 60.

The optical fiber 70 is, for example, housed in the transducer case 80 and disposed in the distal end side (the front side) of the light source 60. The optical fiber 70 is disposed to be spaced from the light source 60. The optical fiber 70 guides and emits the light received from the light source 60 forward with respect to the distal end 71. The optical fiber 70 is linearly formed and disposed so as to extend in the axial direction of the ultrasonic transducer 100. The optical fiber 70 is inserted through the first hole 21, the second hole 31, and the third hole 51, and passes through the piezoelectric element 20, the acoustic matching layer 30, and the backing material 50. On the other hand, as described above, the optical fiber 70 does not pass through the acoustic lens 40. As described above, even though the distal end 71 of the optical fiber 70 abuts on the rear surface 42 of the acoustic lens 40, the distal end 71 of the optical fiber 70 may be spaced from the acoustic lens 40.

Note that the light source 60 and the optical fiber 70 are not limited to have the above-described configuration. For example, instead of being individually formed and arranged spaced, the light source 60 and the optical fiber 70 may be disposed such that both are integrated or disposed integrally. The light source 60 may be disposed outside the transducer case 80. In this case, a member for guiding the light of the light source 60 up to the optical fiber 70 may be attached in the ultrasonic transducer 100, or the base end portion of the optical fiber 70 may be extended and curved so as to be stretched out to the light source 60. The optical fiber 70 is not limited to be linearly formed but it is only necessary to be configured such that the light of the light source 60 is guided up to a back surface of the light emission surface 10b of the acoustic lens 40, and thus, may be formed, for example, into a curved line.

The transducer case 80 is formed such that the transducer case 80 can house the piezoelectric element 20, the acoustic matching layer 30, the acoustic lens 40, the backing material 50, the light source 60, and the optical fiber 70. The transducer case 80 is formed, for example, of a resin with an insulation property. The transducer case 80 houses and holds the piezoelectric element 20, the acoustic matching layer 30, the acoustic lens 40, the backing material 50, the light source 60, and the optical fiber 70. The transducer case 80 is, for example, formed to have rigidity with which, for example, a deformation does not occur when a user grips the ultrasonic transducer 100. The cable CA is extracted from the base end portion (a rear portion) of the transducer case 80 (see FIG. 1).

The ultrasonic transducer 100 according to the above-described embodiment does not have a protective coating, such as a polyparaxylylene coating, on the surface. However, the ultrasonic transducer 100 may have a configuration with the above-described protective coating, and, in such a case, the protective coating may be formed on, for example, a surface including the front surface 41 of the acoustic lens 40.

Next, the following describes an example of a specific operation of the ultrasonic transducer 100 when the ocular axial length is measured. When the measurement of the ocular axial length is performed using the ultrasonic transducer 100, the abutting surface 10 of the ultrasonic transducer 100 is abutted on the eyeball (the subject).

In a state where the eyeball abuts on the abutting surface 10, the ultrasonic sound wave is transmitted toward the eyeball from the ultrasonic transducer 100. This ultrasonic sound wave is generated in the piezoelectric element 20, transmitted through the acoustic matching layer 30 and the acoustic lens 40 in this order, and then, transmitted via the ultrasonic sound wave transmitting and receiving surface 10a (see FIG. 2).

In a state where the eyeball abuts on the abutting surface 10, the eyeball is irradiated with a light from the ultrasonic transducer 100. This light is generated in the light source 60, transmitted through the optical fiber 70 and the acoustic lens 40 in this order, and then, emitted via the light emission surface 10b (see FIG. 2).

The ultrasonic sound wave reflected by the eyeball is received by the ultrasonic transducer 100 via the ultrasonic sound wave transmitting and receiving surface 10a. This received wave is transmitted through the acoustic lens 40 and the acoustic matching layer 30 in this order and reaches the piezoelectric element 20. The received wave is converted into the electrical signal in the piezoelectric element 20 and transmitted to the cable CA (see FIG. 1).

As described above, the acoustic lens 40, which converges the ultrasonic sound wave, is disposed on the distal end 100a of the ultrasonic transducer 100 according to the above-described embodiment. While conventional piezoelectric element and acoustic matching layer have been made into a shape having a depressed surface with a predetermined curvature in order to converge the ultrasonic sound wave, the piezoelectric element 20 and the acoustic matching layer 30 are not necessarily made into the shape having the depressed surface since the above-described embodiment is configured to include the acoustic lens 40. The piezoelectric element 20 and the acoustic matching layer 30 of the above-described embodiment are in a plate shape having a planar surface, thereby ensuring an easy production compared with the one in the shape having the depressed surface. This ensures easily producing the ultrasonic transducer 100.

According to the above-described embodiment, the acoustic lens 40 is formed to have a predetermined thickness from a material with the withstand voltage (insulation property) such that the ultrasonic transducer 100 has the withstand voltage. In the conventional one, the withstand voltage has been ensured, in particular, in a portion surrounded by the opening portion 81 of the transducer case 80 by thickly forming the acoustic matching layer 30 and forming a protective coating whose main raw material is the polyparaxylylene on the acoustic matching layer 30. Meanwhile, in the above-described embodiment, since the acoustic lens 40 is disposed in the ultrasonic transducer 100, a range that can be set for the thickness T of the acoustic matching layer 30 can be expanded in a thinning direction (the thickness T can be made thinner) by the thickness of the acoustic lens 40, and the ultrasonic transducer 100 can be constituted without including the protective coating. This ensures easily setting the thickness T of the acoustic matching layer 30 to a thin thickness of, for example, $\lambda/4$. Since the ultrasonic transducer 100 according to the above-described embodiment does not have such a protective coating, a film formation process of the protective coating is not necessary in a production process of the ultrasonic transducer 100, thereby ensuring producing the ultrasonic transducer 100 at a low cost. Since the thickness T of the acoustic matching layer 30 is set to $\lambda/4$, a satisfactory acoustic matching can be made in the acoustic matching layer 30 compared with a case where the thickness T is set to another value.

According to the above-described embodiment, the transparent acoustic lens 40 is disposed on the distal end 71 side of the optical fiber 70, and the ultrasonic sound wave transmitting and receiving surface 10a and the light emission surface 10b are formed on an identical curved surface. This configuration facilitates forming the abutting surface 10 smooth in the configuration of the ultrasonic transducer with which a light is emitted from the abutting surface 10. That is, since the acoustic lens 40 is arranged in the distal end 71 side of the optical fiber 70, the presence of the optical fiber 70 prevents a level difference or the like from being formed on the abutting surface 10, thereby ensuring easily forming the smooth abutting surface 10 on the acoustic lens 40. Since the acoustic lens 40 is transparent, the light emitted from the optical fiber 70 is efficiently transmitted through the acoustic lens 40.

Figure 5A:
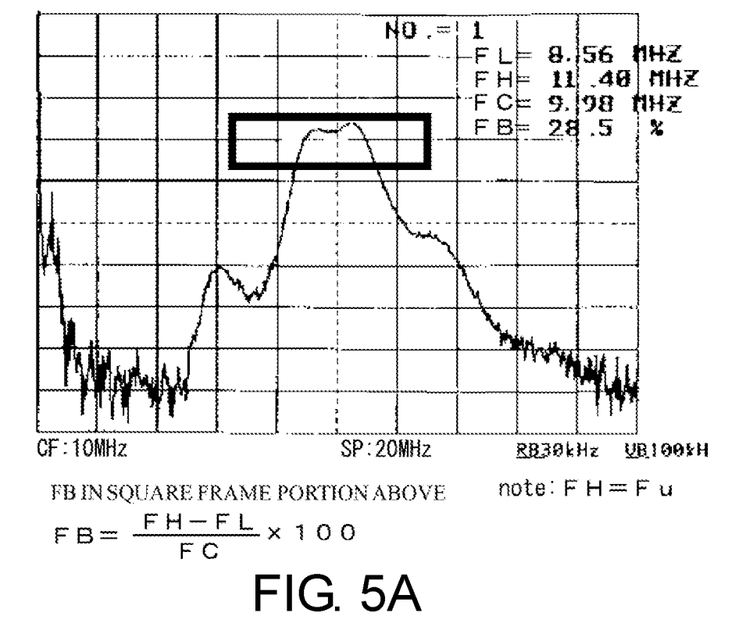
FIG. 5A and FIG. 5B are drawings illustrating intensities of reflected echoes of the ultrasonic transducers.
Figure 5B:
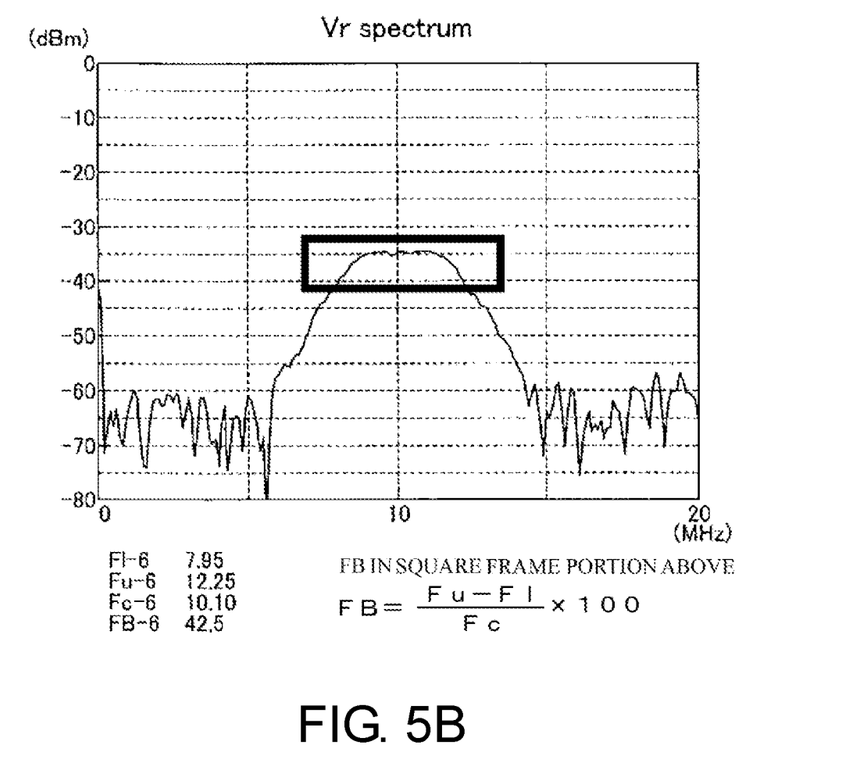

Subsequently, the following describes a measurement result of intensity (level) of reflected echo (received wave) received by the ultrasonic transducer. FIG. 5A and FIG. 5B are drawings illustrating the intensities of the reflected echoes of the ultrasonic transducers. FIG. 5A is a comparative example and FIG. 5B is a drawing illustrating a measurement result of the ultrasonic transducer 100 of the embodiment. In FIG. 5A and FIG. 5B, the vertical axis is the intensity of the reflected echo (unit: dBm) and one square represents 5 dB. The horizontal axis is a frequency (unit: MHz). FIG. 5A and FIG. 5B illustrate the intensities of the reflected echoes in a range from 0 MHz to 20 MHz. Note that the comparative example in FIG. 5A was measured using an ultrasonic transducer of a conventional type. While the polyparaxylylene coating is not applied to the ultrasonic transducer 100 of the embodiment, the polyparaxylylene coating is applied to the above-described conventional typed ultrasonic transducer.

In the above-described measurement, the reflected echoes received by the ultrasonic transducers were observed using a spectrum analyzer. Then, fractional bandwidths (FB) were calculated using the measurement data in FIG. 5A and FIG. 5B. A calculation method and calculation results of the fractional bandwidths are as follows.

First, when frequencies at points decreased by 6 dB from the peak (the maximum level point) of the observed reflected echo are FL and FH, a center frequency (FC) (sometimes represented as "Fc") is defined by a formula, $FC=(FL+FH)/2$ [MHz]. Here, FL (Lower Frequency) (sometimes represented as "Fl") is a $-6$ dB lower limit frequency. FH (Higher Frequency) is also Fu (upper Frequency) and is a $-6$ dB upper limit frequency.

Next, fractional bandwidths (FB) were defined by a formula, $FB=(FH-FL)/FC \times 100$ [%] and the fractional bandwidths were calculated. Specifically, the fractional bandwidth of the comparative example in FIG. 5A is calculated to be $(11.40-8.56)/9.98 \times 100\% = 28.5\%$ from the above-described formula. Similarly, the fractional bandwidth in FIG. 5B is calculated to be $(12.25-7.95)/10.10 \times 100\% = 42.5\%$ from the formula of $FB=(Fu-Fl)/Fc \times 100[\%]$.

From the above-described results, the fractional bandwidth of the ultrasonic transducer 100 in FIG. 5B is 42.5% and is wide compared with the fractional bandwidth (28.5%) of the comparative example (the measurement result of the conventional typed ultrasonic transducer) in FIG. 5A. As illustrated in FIG. 5A and FIG. 5B, the fractional bandwidth of the ultrasonic transducer 100 has the −6 dB lower limit frequency (FL) wide in a low frequency side and the −6 dB upper limit frequency (Fu, FH) wide in a high frequency side compared with the comparative example. As a result, the ultrasonic transducer 100 of the embodiment is confirmed to have a wide fractional bandwidth compared with the conventional typed ultrasonic transducer, thereby improving the property.

The ultrasonic transducer 100 of the embodiment has a short pulse width in a received waveform compared with that of the conventional typed ultrasonic transducer. Here, the pulse width is a time at which ringing (distortion of signal waveform) becomes equal to or less than $1/10$ (−20 dB), $1/100$ (−40 dB), and $1/1000$ (−60 dB) with respect to a crest value of the reflected echo (the received echo). This causes the ultrasonic transducer 100 of the embodiment to have a good distance resolution compared with that of the conventional typed ultrasonic transducer, thereby improving the property.

While the embodiment of the ultrasonic transducer according to the disclosure has been described above, the disclosure is not limited to the embodiment described above. A variety of variations can be made within a range not departing from a gist of the disclosure. One or more requirements described in the above-described embodiment may be omitted. Such variations, modifications, or omitted embodiments are also encompassed by the technical scope of the disclosure.

In the above-described embodiment, the piezoelectric element 20 has been formed from a round type PZT, but it is not limited to this. For example, a shape of the piezoelectric element 20 may have an end surface in the thickness direction in a curved plate shape formed into a depressed shape or in a prism-shape. A material that constitutes the piezoelectric element 20 may be barium titanate ($BaTiO_3$), lead titanate ($PbTiO_3$), a piezoelectric thin film, a piezoelectric polymer film, or the like.

In the above-described embodiment, the acoustic matching layer 30 is formed of a disk-shaped epoxy resin, but it is not limited to this. For example, the shape of the acoustic matching layer 30 may have an end surface in the thickness direction in a curved plate shape formed into a depressed shape or in a prism-shape, instead of being formed into a disk-shape having a planar surface overlapping on the piezoelectric element 20.

In the above-described embodiment, the thickness T of the acoustic matching layer 30 in the direction in which the ultrasonic sound wave is transmitted is set to $\lambda/4$, but it is not limited to this, and the thickness T may be set to, for example, $\lambda/2$.

In the above-described embodiment, the first hole 21, the second hole 31, and the third hole 51 are formed in the central portions of the piezoelectric element 20, the acoustic matching layer 30, and the backing material 50, respectively, and the optical fiber 70 is inserted through the first hole 21, the second hole 31, and the third hole 51, but it is not limited to this. For example, the above-described first to third holes 21, 31, and 51 may be formed in peripheral portions instead of the central portions of the piezoelectric element 20 and the like or may be configured such that only the light passes through the holes without the optical fiber 70 inserted through.

The above-described embodiment includes the optical fiber 70, but whether the optical fiber 70 is included or not is optional, and, for example, it may be configured such that the light of the light source 60 is directly transmitted up to the light emission surface 10b without the optical fiber 70.

According to an aspect of this disclosure, there is provided an ultrasonic transducer including a piezoelectric element in round shape, an acoustic lens, and an acoustic matching layer. The piezoelectric element generates an ultrasonic sound wave. The acoustic lens is for converging the ultrasonic sound wave. The acoustic matching layer is for decreasing a reflection of the ultrasonic sound wave from a subject. The piezoelectric element has a center having a hole through which an optical fiber that guides a light of a light source passes. The ultrasonic transducer transmits and receives the ultrasonic sound wave while emitting the light. The optical fiber is disposed such that a distal end of the optical fiber does not pass through the acoustic lens. The acoustic lens has a color of transparency or semitransparency and a shape in a depressed surface such that the light of the distal end of the optical fiber reaches the subject.

Furthermore, according to an aspect of this disclosure, there is provided an ultrasonic transducer including a piezoelectric element in round shape, an acoustic lens, and an acoustic matching layer. The piezoelectric element generates an ultrasonic sound wave having a wavelength $\lambda$. The acoustic lens is for converging the ultrasonic sound wave. The acoustic matching layer is for decreasing a reflection of the ultrasonic sound wave from a subject. The piezoelectric element has a center having a hole through which an optical fiber that guides a light of a light source passes. The ultrasonic transducer transmits and receives the ultrasonic sound wave while emitting the light. The acoustic lens has a material using a resin with a withstand voltage, mainly polymethylpentene. The acoustic matching layer has a thickness set to $\lambda/4$ by not using a polyparaxylylene coating for ensuring the withstand voltage of the acoustic matching layer. The piezoelectric element and the acoustic matching layer have shapes in a planar surface. The optical fiber is disposed such that a distal end of the optical fiber does not pass through the acoustic lens. The acoustic lens is transparent or semitransparent and has a shape in a depressed surface such that the light of the distal end of the optical fiber reaches the subject.

With the disclosure, a design limitation related to, for example, the piezoelectric element, the acoustic matching layer, and the protective coating, can be decreased in the ultrasonic transducer. With the disclosure, the ultrasonic transducer can be easily produced at a low cost. Furthermore, with the disclosure, the ultrasonic transducer can have a function to emit the light via the abutting surface with the subject and easily form the smooth abutting surface. The polymethylpentene used for the acoustic lens in the ultrasonic transducer of the disclosure has the withstand voltage, the biocompatibility, and the chemical resistance, similarly to the polyparaxylylene.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An ultrasonic transducer, comprising:
a piezoelectric element in a round shape that generates an ultrasonic sound wave having a wavelength λ;
an acoustic lens that converges the ultrasonic sound wave; and
an acoustic matching layer that decreases a reflection of the ultrasonic sound wave from a subject,
wherein the piezoelectric element has a center having a hole through which an optical fiber that guides a light of a light source passes,
the ultrasonic transducer transmits and receives the ultrasonic sound wave while emitting the light,
the acoustic lens has a material using a resin with a withstand voltage, mainly polymethylpentene,
the acoustic matching layer has a thickness set to λ/4 by not applying a polyparaxylylene coating for ensuring the withstand voltage on the acoustic matching layer,
the optical fiber has a distal end configured not to pass through the acoustic lens, and
the piezoelectric element and the acoustic matching layer have shapes in a planar surface.

2. An ultrasonic transducer, comprising:
a piezoelectric element in a round shape that generates an ultrasonic sound wave;
an acoustic lens that converges the ultrasonic sound wave; and
an acoustic matching layer that decreases a reflection of the ultrasonic sound wave from a subject,
wherein the piezoelectric element has a center having a hole through which an optical fiber that guides a light of a light source passes,
the ultrasonic transducer transmits and receives the ultrasonic sound wave while emitting the light,
the optical fiber is disposed such that a distal end of the optical fiber does not pass through the acoustic lens, and
the acoustic lens has a color of transparency or semitransparency and a shape in a depressed surface such that the light of the distal end of the optical fiber reaches the subject.

3. An ultrasonic transducer, comprising:
a piezoelectric element in a round shape that generates an ultrasonic sound wave having a wavelength λ;
an acoustic lens that converges the ultrasonic sound wave; and
an acoustic matching layer that decreases a reflection of the ultrasonic sound wave from a subject,
wherein the piezoelectric element has a center having a hole through which an optical fiber that guides a light of a light source passes,
the ultrasonic transducer transmits and receives the ultrasonic sound wave while emitting the light,
the acoustic lens has a material using a resin with a withstand voltage, mainly polymethylpentene,
the acoustic matching layer has a thickness set to λ/4 by not using a polyparaxylylene coating for ensuring the withstand voltage of the acoustic matching layer,
the piezoelectric element and the acoustic matching layer have shapes in a planar surface,
the optical fiber is disposed such that a distal end of the optical fiber does not pass through the acoustic lens, and
the acoustic lens is transparent or semitransparent and has a shape in a depressed surface such that the light of the distal end of the optical fiber reaches the subject.

* * * * *